(12) United States Patent
Fukui et al.

(10) Patent No.: US 8,901,166 B2
(45) Date of Patent: Dec. 2, 2014

(54) EPIGALLOCATECHIN GALLATE TETRAMER AND VASCULAR ENDOTHELIAL FUNCTION IMPROVING AGENT CONTAINING THE SAME

(75) Inventors: Yuko Fukui, Osaka (JP); Mai Imamoto, Tokyo (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 630 days.

(21) Appl. No.: 13/060,996

(22) PCT Filed: Aug. 28, 2009

(86) PCT No.: PCT/JP2009/065084
§ 371 (c)(1),
(2), (4) Date: Feb. 25, 2011

(87) PCT Pub. No.: WO2010/024393
PCT Pub. Date: Mar. 4, 2010

(65) Prior Publication Data
US 2011/0152361 A1   Jun. 23, 2011

(30) Foreign Application Priority Data

Aug. 29, 2008   (JP) ................. 2008-222935

(51) Int. Cl.
| | | |
|---|---|---|
| *C07D 311/62* | (2006.01) | |
| *A61K 31/353* | (2006.01) | |
| *A23L 1/30* | (2006.01) | |
| *A23L 2/52* | (2006.01) | |

(52) U.S. Cl.
CPC ............ *A61K 31/353* (2013.01); *C07D 311/62* (2013.01); *A23L 1/3002* (2013.01); *A23V 2002/00* (2013.01); *A23L 2/52* (2013.01)
USPC .......................................... 514/456; 549/399

(58) Field of Classification Search
CPC ............................. C07D 311/62; A61K 31/353
USPC .......................................... 549/399; 514/456
See application file for complete search history.

(56) References Cited

U.S. PATENT DOCUMENTS

| | | | |
|---|---|---|---|
| 2008/0275258 A1 | 11/2008 | Nakai et al. | |
| 2009/0186936 A1 | 7/2009 | Moriguchi et al. | |
| 2011/0150790 A1* | 6/2011 | Fukui et al. ................ | 424/55 |
| 2011/0172300 A1* | 7/2011 | Fukui et al. ................ | 514/456 |

FOREIGN PATENT DOCUMENTS

| | | |
|---|---|---|
| JP | 02-187433 A | 7/1990 |
| JP | 10-142726 A | 5/1998 |
| JP | 2009-001531 A | 1/2009 |
| WO | WO-2004030440 A2 | 4/2004 |
| WO | 2005/116005 | 12/2005 |
| WO | WO-2007136015 A1 | 11/2007 |

OTHER PUBLICATIONS

Zhou et al. (J. Agric. Food Chem. 2005, 53, 8614-8617).*
Extended European Search Report dated Apr. 3, 2012 in European Patent Application No. EP09810041.5.
M. Lorenz et al., "A Constituent of Green Tea, Epigallocatechin-3-gallate, Activates Endothelial Nitric Oxide Synthase by a Phosphatidylinositol-3-OH-kinase-, cAMP-dependent Protein Kinase-, and Akt-dependent Pathway and Leads to Endothelial-dependent Vasorelaxation", *Journal of Biological Chemistry*, vol. 279, No. 7, pp. 6190-6195, Nov. 2004.
S. Duffy et al., "Short- and Long-Term Black Tea Consumption Reverses Endothelial Dysfunction in Patients With Coronary Artery Disease", Circulation, *Journal of the American Heart Association*, vol. 104, pp. 151-156, Feb. 2001.
E. Anter et al., "Activation of Endothelial Nitric-oxide Synthase by the p38 MAPK in Response to Black Tea Polyphenols," *Journal of Biological Chemistry*, vol. 279, No. 45, pp. 46637-46643, Aug. 2004.

(Continued)

*Primary Examiner* — Kristin Vajda
*Assistant Examiner* — Valerie Rodriguez-Garcia
(74) *Attorney, Agent, or Firm* — Drinker Biddle & Reath LLP

(57) ABSTRACT

Providing a compound capable of continuously taking and having a vascular endothelial function improving effect by enhancing NO function from the vascular endothelial cells. A compound represented by Formula (I) wherein $R_1$, $R_2$, $R_3$ and $R_4$ are each independently H or a gallate group, a vascular endothelial function improving agent, food and drink or pharmaceutical composition containing the compound.

Formula (I)

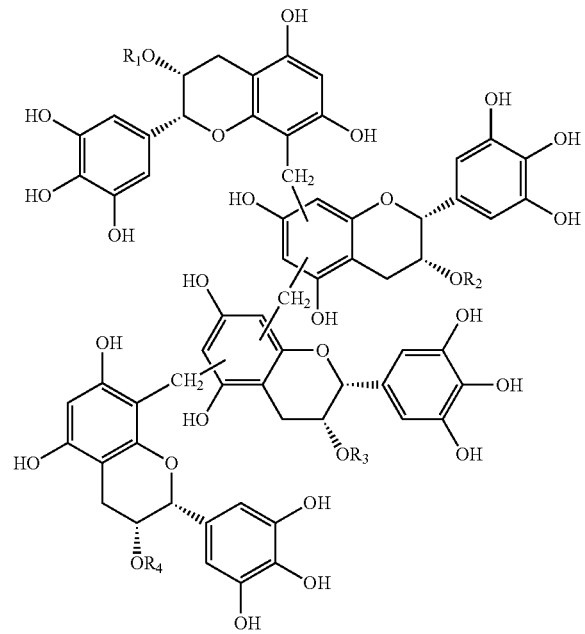

6 Claims, 12 Drawing Sheets

(56) References Cited

OTHER PUBLICATIONS

F. Hashimoto et al., "Tannins and Related Compounds. XC.[1]) 8-C-Ascorbyl (−)-Epigallocatechin 3-O-Gallate and Novel Dimeric Flavan-3-ols, Oolonghomobisflavans A and B, from Oolong Tea. (3)", *Chem. Pharm. Bull.* 37(12), 3255-3263, Dec. 1989.

M. Nakai et al., "Inhibitory Effects of Oolong Tea Polyphenols on Pancreatic Lipase in Vitro", *J. Agric. Food Chem.* 53, 4593-4598, Apr. 2005.

International Search Report mailed Oct. 13, 2009 in PCT/JP2009/065084 filed Aug. 28, 2009.

Folia Pharmacol. Jpn. vol. 125: pp. 285-290 (2005).

Quyyumi et al., "Nitric oxide activity in the human coronary circulation. Impact of risk factors for coronary atherosclerosis", Journal of Clinical investigation, vol. 95: pp. 1747-1755 (1995).

Stas et al., Mineralocorticoid Receptor Blockade Attenuates Chronic Overexpression of the Renin-Angiotensin-Aldosterone System Stimulation of Reduced Nicotinamide Adenine Dinucleotide Phosphate Oxidase and Cardiac Remodeling:, Endocrinology, vol. 148: pp. 3773-3780 (2007).

English Translation of Written Opinion of the International Searching Authority (2011) for PCT/JP2009/065084.

Kubata, et al., "Kola acurninata proanthocyanidins: a class of anti-trypanosomal compounds effective against *Trypanosoma brucei*", International Journal for Parasitology, 35 (1), 2005, pp. 91-103.

Kuliev, et al., "Oligomeric proanthocyanidin glycosides of *Clementsia semenovii* and their biological activity. III", Chemistry of Natural Compounds (Translation of Khimiya Prirodnykh Soedinenii), 36(1), 2000, pp. 60-67.

Khurana et al., "Antiapoptotic Actions of Methyl Gallate on Neonatal Rat Cardiac Myocytes Exposed to H2O2", Oxid Med Cell Logev vol. 2014, Article ID 657512, 9 pages (published Jan. 12, 2014).

\* cited by examiner

EPIGALLOCATECHIN GALLATE TETRAMER AND VASCULAR ENDOTHELIAL FUNCTION IMPROVING AGENT CONTAINING THE SAME

CROSS REFERENCE TO RELATED APPLICATIONS

This application is the National Stage of International Application No. PCT/JP2009/065084, filed Aug. 28, 2009, and claims benefit of Japanese Application No. 2008-222935, filed Aug. 29, 2008, which are herein incorporated by reference in their entirety.

TECHNICAL FIELD

The present invention relates to a novel epigallocatechin gallate tetramer compound, a method for producing the compound, and a food and drink and a pharmaceutical composition containing the compound, particularly a food and drink and a pharmaceutical composition exerting a vascular endothelial function improving action.

BACKGROUND ART

Metabolic syndrome is a pathologic condition in which a visceral fat accumulation amount increases by lifestyle habits and hereditary predisposition, with the result that insulin resistance is induced and symptoms such as lipidosis, hypertension and impaired glucose tolerance emerge and a vascular lesion is likely to occur. Such pathologic condition leads to arteriosclerosis such as cardial infarction and cerebral infarction and at worst may result in death.

When insulin resistance emerges due to metabolic syndrome, the function of the vascular endothelial cells is damaged. As a cause thereof, abnormality of the nitrogen monoxide (hereinafter, simply referred to as NO) production system in the vascular endothelial cells is suggested (Non Patent Literature 1).

NO is produced by L-arginine and an oxygen molecule by endothelial NO synthetase (hereinafter, simply referred to as eNOS) in the vascular endothelial cells. The role of NO, which is a vascular relaxation factor derived from the vascular endothelium, is primarily a suppressive action on proliferative change, inflammatory change, platelet aggregation and oxidation stress. A reduction of NO production and insufficient action thereof were observed in the presence of various risk factors such as arteriosclerosis and hyperlipemia (Non Patent Literature 2). Particularly, in the state of insulin resistance associated with metabolic syndrome, it is known that the activity of GTP cyclohydrase I (hereinafter, simply referred to as GTP-CH1), which is a coenzyme of eNOS, i.e., a tetrahydrobiopterin (hereinafter, simply referred to as $BH_4$) producing enzyme, reduces (Non Patent Literature 1). Mechanism of reduction of NO production and insufficient production thereof is complicated; however, it is known that eNOS activity is inhibited by a metabolite of L-arginine, asymmetric dimethyl arginine (hereinafter, simply referred to as ADMA). Furthermore, in the state where eNOS activity reduces, oxygen molecules are preferentially metabolized by NADPH oxidase to generate active oxygen, which further induces hypoactivity of vascular endothelium (Non Patent Literature 3). On the other hand, when vascular endothelial cells produce ADMA degrading enzyme, i.e., dimethylarginine dimethylaminohydrolase 2 (hereinafter, simply referred to as DDAH 2), the vascular endothelial function can be satisfactorily maintained. Furthermore, the vascular endothelial function can be satisfactorily maintained also by reducing NADPH oxidase activity present in the vascular endothelial cells.

A food material having a vascular endothelial function improving effect, (−)-epigallocatechin-3-O-gallate (hereinafter, also referred to as "EGCG") contained in green tea is known (Non Patent Literature 4). Furthermore, it is reported that when black tea is taken, the vasodilation depending upon blood flow of the human upper arm is improved (Non Patent Literature 5), that eNOS activation is facilitated in the in-vitro study using a black tea extract (Non Patent Literature 6); however, active ingredients thereof did not elucidated. Furthermore, no study has been made on oolong tea and its components.

Examples of the EGCG polymer produced by an oolong tea intrinsic fermentation process include a dimer (oolong homobisflavan A and oolong homobisflavan B)(Non Patent Literature 7) and a trimer (Patent Literature 1) have been isolated and identified. It has been reported that these compounds have strong pancreatic lipase inhibitory activity (Non Patent Literature 8 and Patent Literature 1).

CITATION LIST

Patent Literature

PTL 1: International Publication No. WO2005/116005

Non Patent Literature

NPL 1: Folia Pharmacol. Jpn. Vol. 125: p285-290, 2005
NPL 2: Journal of clinical Investigation, vol. 95, p1747-1755, 1995
NPL 3: Endocrinology, vol. 148, p3773-3780, 2007
NPL 4: Journal of Biological Chemistry, vol. 279, p6190-6195, 2004
NPL 5: Circulation. Vol. 104, p151-156, 2001 NPL 6: Journal of Biological Chemistry, vol. 279, p46637-46643, 2004
NPL 7: Chem. Pharm. Bull. 37(12), 3255-3263, 1989
NPL 8: J. Agric. Food Chem. 53, 4593-4598 (2005)

SUMMARY OF INVENTION

Technical Problem

Non Patent Literature 4 describes the vascular endothelial function improving effect of EGCG; however, in a study using cultured cells, a relatively high concentration of at least 30 to 50 μM is required to increase eNOS activity. Furthermore, Non Patent Literature 5 discloses the vascular endothelial function improving effect of black tea and described that the vasodilation depending upon blood flow of the upper arm is improved in a group where black tea is allowed to take to a human in a dose of 900 ml per day for 4 weeks, compared to a control group.

As described above, EGCG has a vascular endothelial function improving effect; however the effect is not sufficient. To obtain the effect by taking black tea containing EGCG, a relatively large amount of black tea, etc. must be taken. Furthermore, the EGCG is a cause of bitter taste and astringency and thus if EGCG is continuously taken, flavor is a problem. In addition, a large amount of black tea intake leads to intake of a large amount of caffeine. From this, taking black tea is considered improper for continuous intake in order to maintain the vascular endothelial function.

An objective of the present invention is to provide a compound capable of continuously taking and having a vascular endothelial function improving effect by enhancing NO function from the vascular endothelial cells, and further provide a food and drink containing the compound.

Solution to Problem

The present inventors studied with a view to solving these problems on a compound derived from a compound having a chroman ring such as EGCG. As a result, they found that a novel compound having four chroman rings has a more effective vascular endothelial function improving action than EGCG. Based on the finding, the present invention has been accomplished.

More specifically, according to the present invention, there are provided

1. A compound represented by Formula (I):

[Chem. 1]

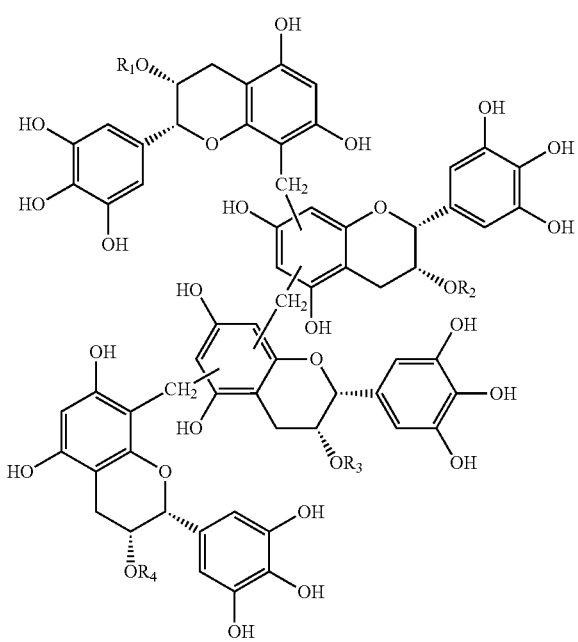

Formula (I)

wherein $R_1$, $R_2$, $R_3$ and $R_4$ are each independently H or a group represented by Formula (A):

[Chem. 2]

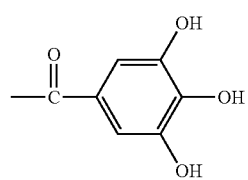

Formula (A)

or a salt thereof;

2. The compound according to item 1 above, represented by Formula (II):

[Chem. 3]

Formula (II)

wherein $R_1$, $R_2$, $R_3$ and $R_4$ are the same as defined above, or a salt thereof;

3. The compound according to item 1 above, represented by Formula (III):

[Chem. 4]

Formula (III)

wherein $R_1$, $R_2$, $R_3$ and $R_4$ are the same as defined above, or a salt thereof;

4. The compound according to any one of items 1 to 3 above, in which $R_1$, $R_2$, $R_3$ and $R_4$ are all a group represented by Formula (A):

[Chem. 5]

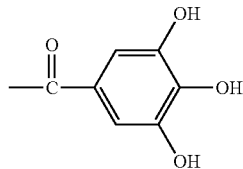

Formula (A)

or a salt thereof;

5. A vascular endothelial function improving agent containing the compound or a salt thereof according to any one of items 1 to 4;

6. A food and drink, in which the compound or a salt thereof according to any one of items 1 to 4 is added;

7. A pharmaceutical composition containing the compound or a salt thereof according to any one of items 1 to 4; and 8. A method for producing the compound according to any one of items 1 to 4, including reacting epigallocatechin gallate or epigallocatechin with formaldehyde in the presence of an acid.

Advantageous Effects of Invention

The present invention can provide beverages or supplements for improving vascular endothelial function, thereby promoting health by blending tetramers of the invention to foods and drinks. These compounds are highly palatable, since flavor is not damaged even though they are added to a food and drink, and excellent in safety and thus can be continuously taken for maintaining a vascular endothelial function.

DESCRIPTION OF EMBODIMENTS

Figure 1:
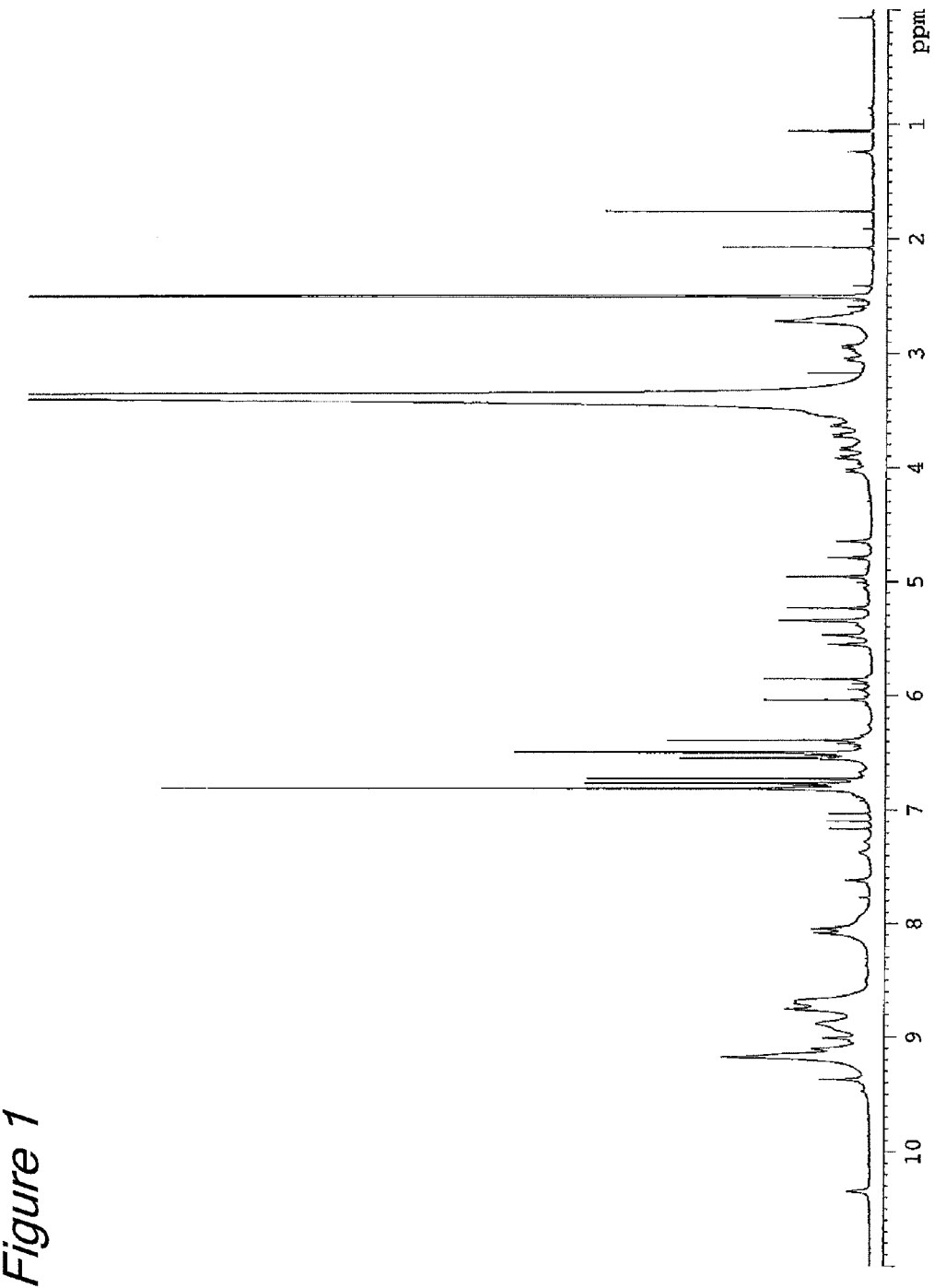
FIG. 1 shows a $^1$H NMR spectrum of compound 1.

The present invention relates to a novel EGCG tetramer compound in which four chroman rings are bonded by a methylene group and represented by Formula (I), a method for producing the compound of Formula (I), and a vascular endothelial function improving agent, food and drink and pharmaceutical composition containing the compound of Formula (I). The present invention will be described below.
<EGCG Tetramer Compound>

An EGCG tetramer compound of the present invention represented by Formula (I) can be produced as follows.

The compound of Formula (I) in which $R_1$, $R_2$, $R_3$ and $R_4$ each are a group (gallate group) represented by Formula (A) can be produced by reacting (−)-epigallocatechin-3-O-gallate with formaldehyde in a solvent in the presence of an acid.

Examples of the solvent that can be used in the reaction include alcohols such as methanol, ethanol, n-propanol and isopropanol. The use amount of solvent is not particularly limited; however, for example, 20 to 200 parts by mass of solvent can be used relative to 1 part by mass of EGCG.

Examples of the acid that can be used herein include inorganic acids such as hydrochloric acid, sulfuric acid and nitric acid and organic acids such as formic acid and acetic acid. The use amount of acid is not particularly limited; however, 0.01 to 2 moles of acid can be used relative to 1 mole of EGCG.

The amount of formaldehyde that can be used is, for example, 1 to 100 moles relative to 1 mole of EGCG.

Reaction temperature and time vary depending upon e.g., the amount of solvent to be used; however, for example, reaction temperature is −10 to 50° C., and reaction time is 0.2 to 12 hours. Typically, the reaction temperature is room temperature (about 25° C.).

The compound of Formula (I) in which $R_1$, $R_2$, $R_3$ and $R_4$ each are H (hydrogen atom) can be produced by reacting (−)-epigallocatechin in place of (−)-epigallocatechin-3-O-gallate with formaldehyde in the same manner as above.

Note that when (−)-epigallocatechin-3-O-gallate or (−)-epigallocatechin is used in the reaction with formaldehyde, in the resultant compound of Formula (I), a substituent at position 2 of each chroman ring and a substituent at position 3 thereof form cis relative configuration.

A tetramer product is obtained by the reaction between (−)-epigallocatechin-3-O-gallate or (−)-epigallocatechin and formaldehyde generally as a mixture of tetramer compounds containing at least two of three compounds represented by Formula (II), Formula (III) and Formula (IV) different in coupling scheme of chroman rings by a methylene group. From such a mixture, compounds of Formula (II), Formula (III) and Formula (IV) each can be isolated by use of a known purification method such as open column chromatography using a styrene based adsorption resin such as HP-20 (manufactured by Mitsubishi Chemical Corporation) and a dextran based resin such as Shephadex LH-20, and high performance liquid chromatography (HPLC).

[Chem. 6]

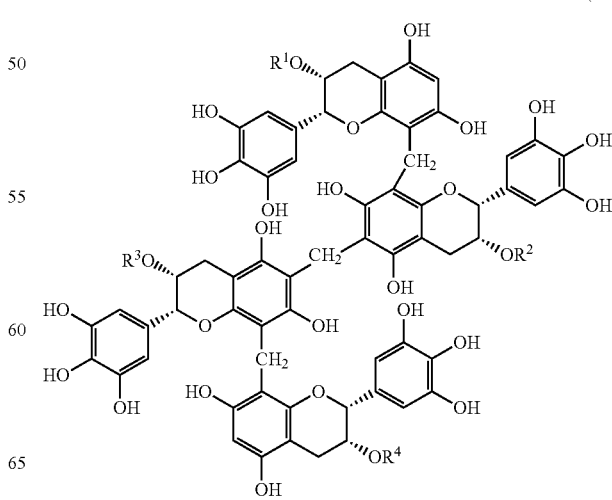

Formula (IV)

The compound of Formula (I), wherein 1 to 4 of $R_1$, $R_2$, $R_3$ and $R_4$ are H, can be also produced by removing the gallate group from the compound of Formula (I) wherein $R_1$, $R_2$, $R_3$ and $R_4$ each are a gallate group by hydrolysis. Such hydrolysis is performed by use of an aqueous solution of a basic compound such as sodium hydroxide and potassium hydroxide or by use of a hydrolytic enzyme such as an enzyme having tannase activity.

In such hydrolysis, 1, 2, 3 or 4 gallate groups are removed from the compound of Formula (I) wherein $R_1$, $R_2$, $R_3$ and $R_4$ each are a gallate group to provide a mixture of a plurality of compounds. In this case, individual compounds can be isolated from the mixture by use of a known purification method such as open column chromatography using a styrene based adsorption resin including HP-20 (manufactured by Mitsubishi Chemical Corporation) and a dextran based resin such as Shephadex LH-20 and high performance liquid chromatography (HPLC).

The present invention also relates to a salt of the compound of Formula (I).

Such a salt is not particularly limited as long as it is a salt that can be formed from a compound of Formula (I); however, a pharmaceutically acceptable salt is preferable.

Examples thereof include a metal salt with a metal element belonging to the first or second family of the periodic table, such as a lithium salt, a sodium salt, a potassium salt, a calcium salt and a magnesium salt of a compound of Formula (I). Such a metal salt can be formed with, for example, a hydroxide group of a compound of Formula I (a phenolic hydroxide group, a hydroxide group in the case where one or all of $R_1$, $R_2$, $R_3$ and $R_4$ are H).

For example, in a non-protic solvent, the compound of Formula (I) and metallic sodium or sodium hydride are reacted to convert a hydroxide group (—OH) to a sodium alkoxide group (—ONa) to produce a sodium salt of a compound of Formula (I). Furthermore, all hydroxide groups contained in the compound of Formula (I) can be converted into sodium alkoxide groups or only part of the hydroxide groups can be converted into sodium alkoxide groups by controlling the use amount of metallic sodium or sodium hydride.

The compound of Formula (I) of the present invention is a novel compound. When studies were conducted using the compounds of Formula (II) and Formula (III) produced by the present inventors, as standards, it was found that the compounds of Formula (II) and Formula (III) are also present in oolong tea, as described later in Examples. Therefore, the compounds of Formula (II) and Formula (III) can be isolated from tea using *Camellia sinensis* as a raw material, preferably from fermented tea such as oolong tea, black tea and roasted tea by extraction and purification.

Isolation of the compounds of Formula (II) and Formula (III) from these teas can be performed by, for example, adsorption column chromatography and high performance liquid chromatography (HPLC).

<Vascular Endothelial Function Improving Agent, Food and Drink and Pharmaceutical Composition>

A compound of the present invention exerts a vascular endothelial function improving action.

More specifically, a compound of the present invention exerts a vascular endothelial function improving action by enhancing expression of eNOS gene, by enhancing expression of GTP-CH1 gene, by enhancing expression of DDAH2 gene and/or by reducing NADPH oxidase gene. Expression of eNOS gene, GTP-CH1 gene, DDAH2 gene and NADPH oxidase gene can be evaluated by a known method described in literatures or by the method described in Examples below.

As described above, since a compound of the present invention exerts a vascular endothelial function improving action, it can be used as a vascular endothelial function improving agent. Furthermore, since a compound of the present invention exerts a vascular endothelial function improving action, if a compound of the present invention is formed into a dosage form suitable for intake by mammals such as a human by blending it to a food and drink or preparing it into a pharmaceutical composition, the vascular endothelial function improving action can be exerted by using the food and drink or the pharmaceutical product in mammals.

Therefore, the present invention also relates to a food and drink in which a compound of the present invention or a salt thereof is added, and a pharmaceutical composition containing a compound of the present invention or a salt thereof.

A compound of the present invention can be added to various types of foods and drinks. A food and drink to which a compound of the present invention is to be added is not particularly limited. A compound of the present invention can be added to various types of foods and drinks conventionally available. Examples of the foods and drinks include beverages such as refreshing drinks, tea drinks, liquid tonic medicines, healthy drinks, nutrition drinks, sports drinks and carbonated drinks (including concentrated stock solutions and preparatory powders of these beverages) and foods such as gums, candies, jellies, tablets, health foods, nutrition foods and supplements. A compound of the present invention can be added such that the ratio of the compound of the present invention in these foods and drinks becomes, for example, 0.01 to 10000 ppm (μg/ml), preferably 0.06 to 2000 ppm and further preferably 0.1 to 1000 ppm.

When a compound of the present invention is used as a medicinal drug, the medicinal drug can be provided in dosage form of powder, grain, tablet, capsule, liquid and injection. A compound of the present invention or a salt thereof can be orally administered directly or by diluting it with water or the like. Alternatively, it is formed into a preparation with a known carrier for a medicinal drug. For example, a compound of the present invention or a salt thereof can be administered as a peroral liquid preparation such as a syrup agent. Alternatively, if the compound of the present invention or a salt thereof is processed into an extract or a powder and blended with a pharmaceutically acceptable carrier, it can be provided as a peroral solid preparation such as a tablet, a capsule, a grain, and a powder. Examples of the pharmaceutically acceptable carrier include various types of organic or inorganic carrier substances conventionally used as a preparation material. The carrier is blended as an excipient, a lubricant, a binding agent and a disintegrator in a solid preparation and as e.g., a solvent, an excipient, a suspension agent and a binding agent in a liquid preparation. Furthermore, if necessary, additives for a preparation such as an antiseptic agent, an antioxidative agent, a coloring agent and a sweetening agent can be also used.

Furthermore, an effective dose thereof can be appropriately determined depending upon the age and body weight of a patient, the type and significance of a disease and the administration route.

EXAMPLES

The present invention will be more specifically described by way of Examples; however, the present invention is not limited by these.

Example 1

Synthesis and Isolation of Compounds of Formula (II) and Formula (III)

A. Synthesis and Fractionation by Open Column:

Six grams (13 millimole) of (−)-epigallocatechin-3-β-gallate (EGCG) (Teavigo™ manufactured by Roche) was dissolved in 120 ml of ethanol solution (0.02N, 2.4 millimole in terms of HCl), and a formaldehyde ethanol solution (180 ml) (4% by mass, 240 millimole in terms of formaldehyde) was added and then stirred at room temperature for 4 hours. After completion of the reaction, the resultant reaction solution was diluted 10 fold with pure water and loaded on an adsorption resin CHP-20P column (600 ml, 37-75 μm, manufactured by Mitsubishi Chemical Corporation). After washed with water (1200 mL), elution was performed sequentially with 900 ml of a 25 V/V % aqueous acetonitrile solution and 1200 mL of a 30% V/V % aqueous acetonitrile solution. The fraction eluted with the 25V/V % aqueous acetonitrile solution was separated into three fractions (fr. 1 to fr. 3) of 300 ml for each, whereas the faction eluted with the 30% V/V % aqueous acetonitrile solution was separated into four fractions (fr 0.4 to fr. 7) of 300 ml for each.

B. Preparative HPLC Conditions:

The fractionated products obtained by the CHP-20P column purification was further purified by reverse-phase preparative HPLC.

<Conditions>

Column: Develosil ODS-HG-5 (5 cm ϕ×50 cm, manufactured by Nomura Chemical Co., Ltd.)

Mobile phase A: 0.05 V/V % TFA/$H_2O$ (TFA: trifluoroacetic acid),

Mobile phase B: 90 V/V % $CH_3CN$, 0.05 V/V % TFA/$H_2O$,

Flow rate: 32 ml/min

Gradient program: A/B=80/20 (30 minutes), A/B=80/20→60/40 (100 minutes), A/B=60/40 (30 minutes)

Detector: UV ray/visible light adsorption detector, SPD-6AV (manufactured by Shimadzu Corporation)

Detection wavelength: A280 nm

Sample: fr. 2 to fr. 7 obtained by CHP-20P column purification each were dissolved in a 20 V/V % aqueous acetonitrile solution and the total amount was loaded by several times.

<Fraction>

In the above analysis conditions, individual peaks corresponding to retention time 109 minutes (compound 1), 113 minutes (compound 2), 85 minutes (compound 3), 106 minutes (compound 4) and retention time 104 minutes (compound 5) and retention time 135 minutes (compound 6) were collected.

C. Structural Analysis of Compound:

The compounds isolated by preparative HPLC were subjected to MS and NMR measurements.

Ms of compounds 3 to 6 were measured by Q-TOF Premier (manufactured by Micromass, UK) in a negative, V mode. As a result, ion peaks were observed respectively at m/z 927.160, 927.163, 1397.248 and 927.161 [M-H]⁻. Furthermore, NMR spectrum data of compound 3 coincided with the NMR spectrum data of oolong homobisflavan-A described in the literature (Chem. Pharm. Bull 37(12), 3255-3563 (1989)). The NMR spectrum data of compound 4 coincided with the NMR spectrum data of oolong homobisflavan-B described in the literature (Chem. Pharm. Bull 37(12), 3255-3563 (1989)). Furthermore, the NMR spectrum of compound 5 coincided with the NMR spectrum described in FIG. 4 and FIG. 5 of International Publication No. WO 2005/116005. The NMR spectrum of compound 6 coincided with the NMR spectrum described in FIG. 2 and FIG. 3 of International Publication No. WO 2005/116005. From these results, compound 3 was identified as oolong homobisflavan A, compound 4 as oolong homobisflavan-B, compound 5 as the compound represented by the following Formula (V) (wherein R represents a gallate group), and compound 6 as oolong homobisflavan-C.

[Chem. 7]

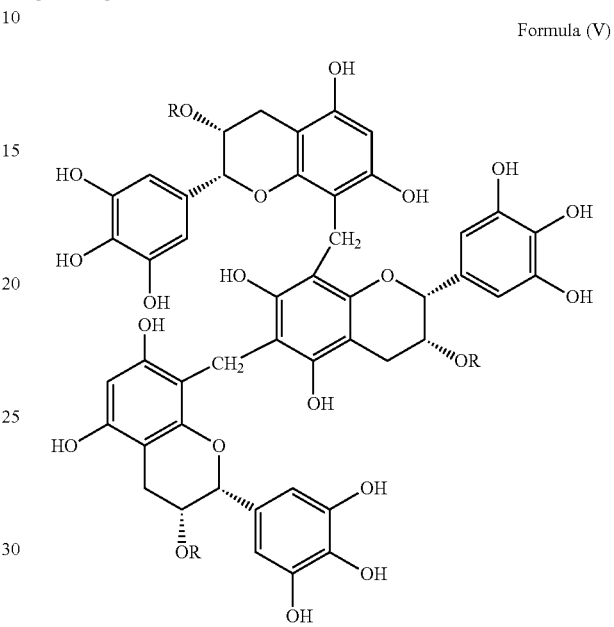

Formula (V)

Compound 1 and compound 2 were subjected to structural analysis by the following MS and NMR.

MS measurement was performed by Q-TOF Premier (manufactured by Micromass, UK) using ESI equipped with a Z spray ion source as an ion source, in a negative, V mode. Mass correction was performed by lock spray at a Cone volt.: 45 V, Capillary voltage: 3 KV, and Source Temp.: 80° C., Desolvation Temp: 180° C. As a reference, leucine enkephalin (m/z 554.2615 [M-H]⁻) was used.

As a result, compound 1 gave molecular ions of m/z 1867.3112 [M-H]⁻ and divalent 933.1517 [M-2H]²⁻ and a molecular formula thereof was calculated as $C_{91}H_{72}O_{44}$ (err.: −11.0 ppm); compound 2 gave molecular ions of m/z 1867.3100 [M-H]⁻ and divalent 933.1151 [M-2H]²⁻ and a molecular formula thereof was calculated as $C_{91}H_{72}O_{44}$ (err.: −11.7 ppm). Either one of the compounds is estimated as a compound having four EGCG molecules crosslinked with three methylene groups.

Figure 2:
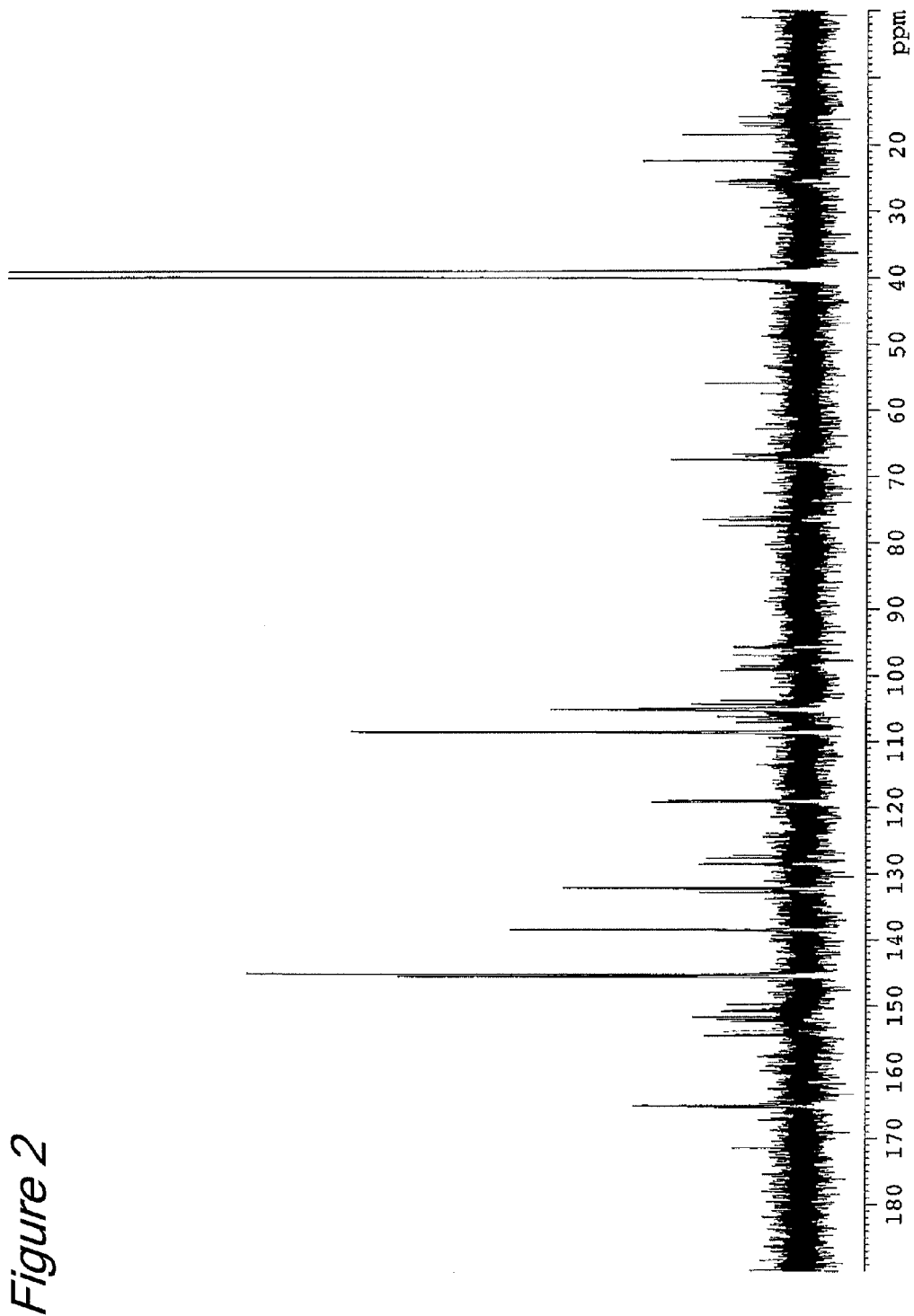
FIG. 2 shows a $^{13}$C NMR spectrum of compound 1.
Figure 3:
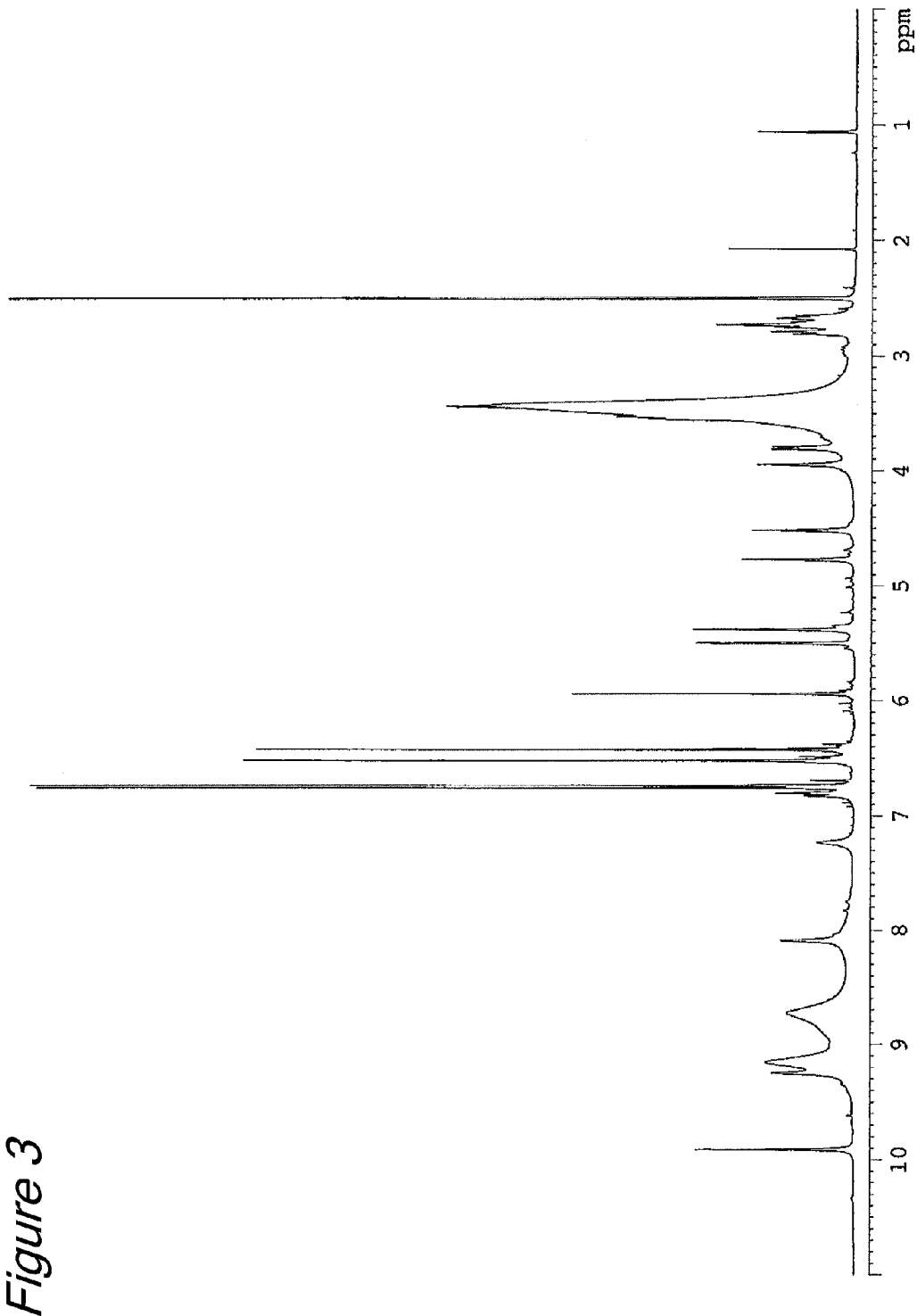
FIG. 3 shows a $^1$H NMR spectrum of compound 2.
Figure 4:
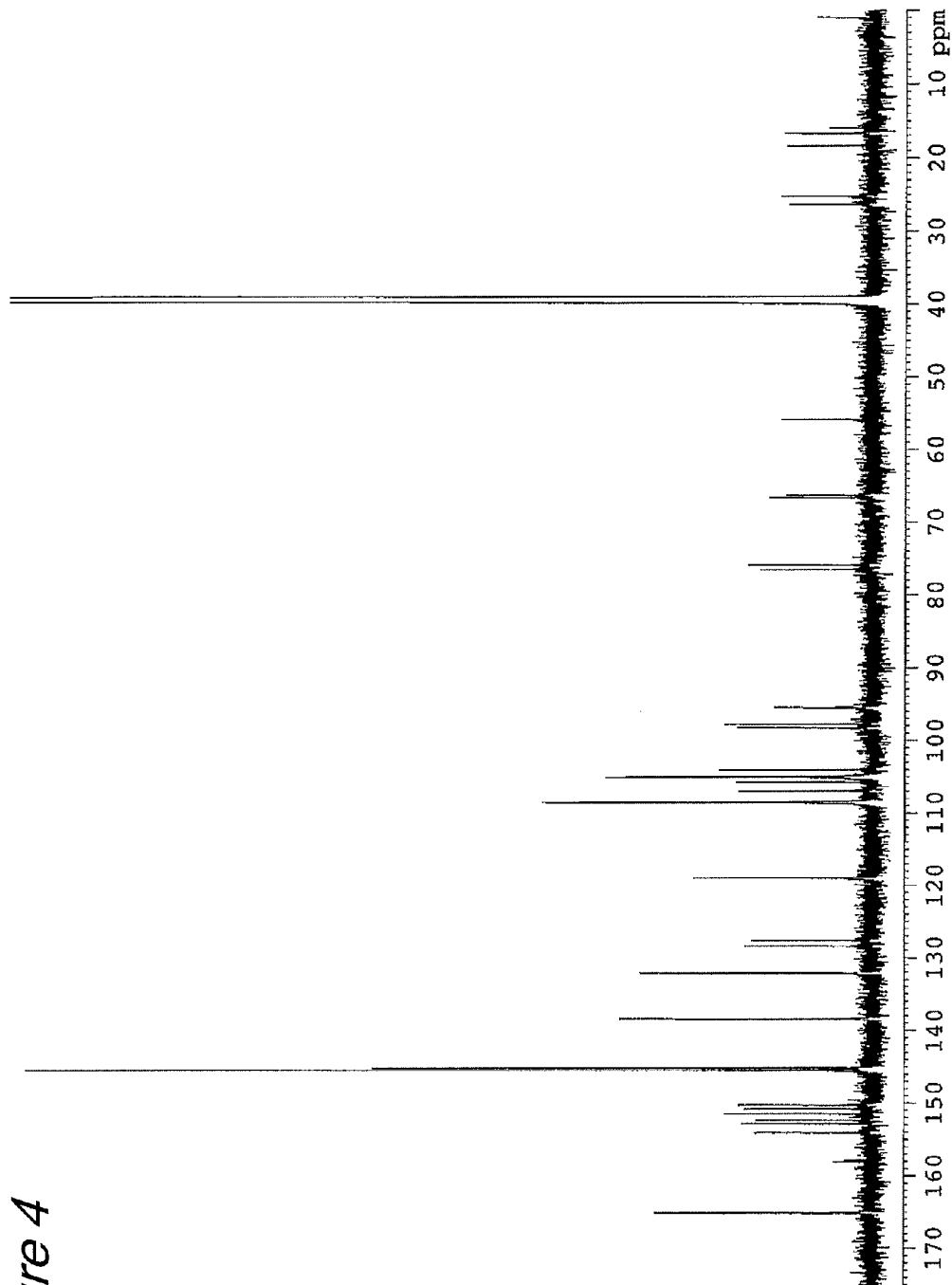
FIG. 4 shows a $^{13}$C NMR spectrum of compound 2.
Figure 5:
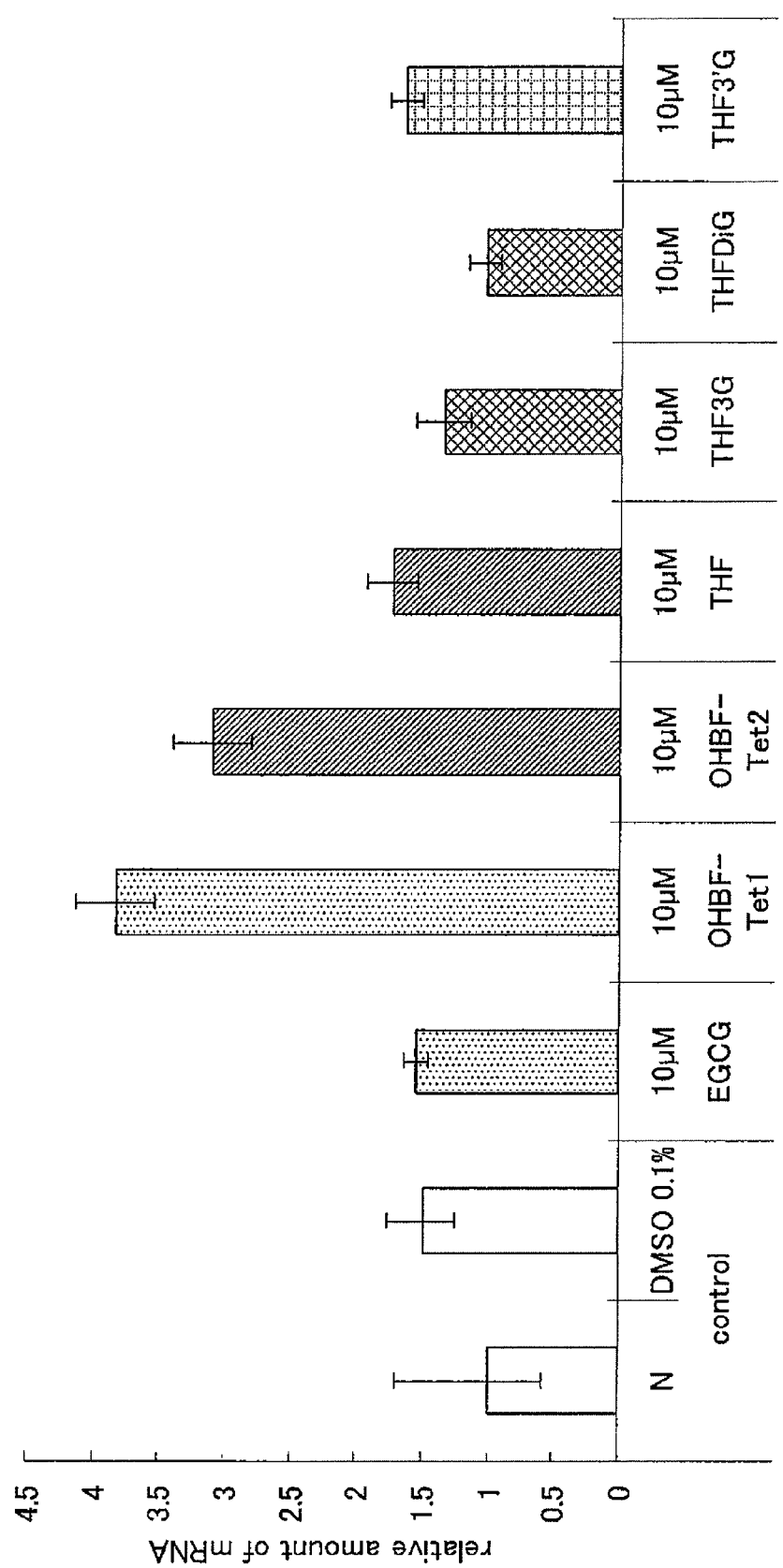
FIG. 5 is a graph showing the results of eNOS expression.
Figure 6:
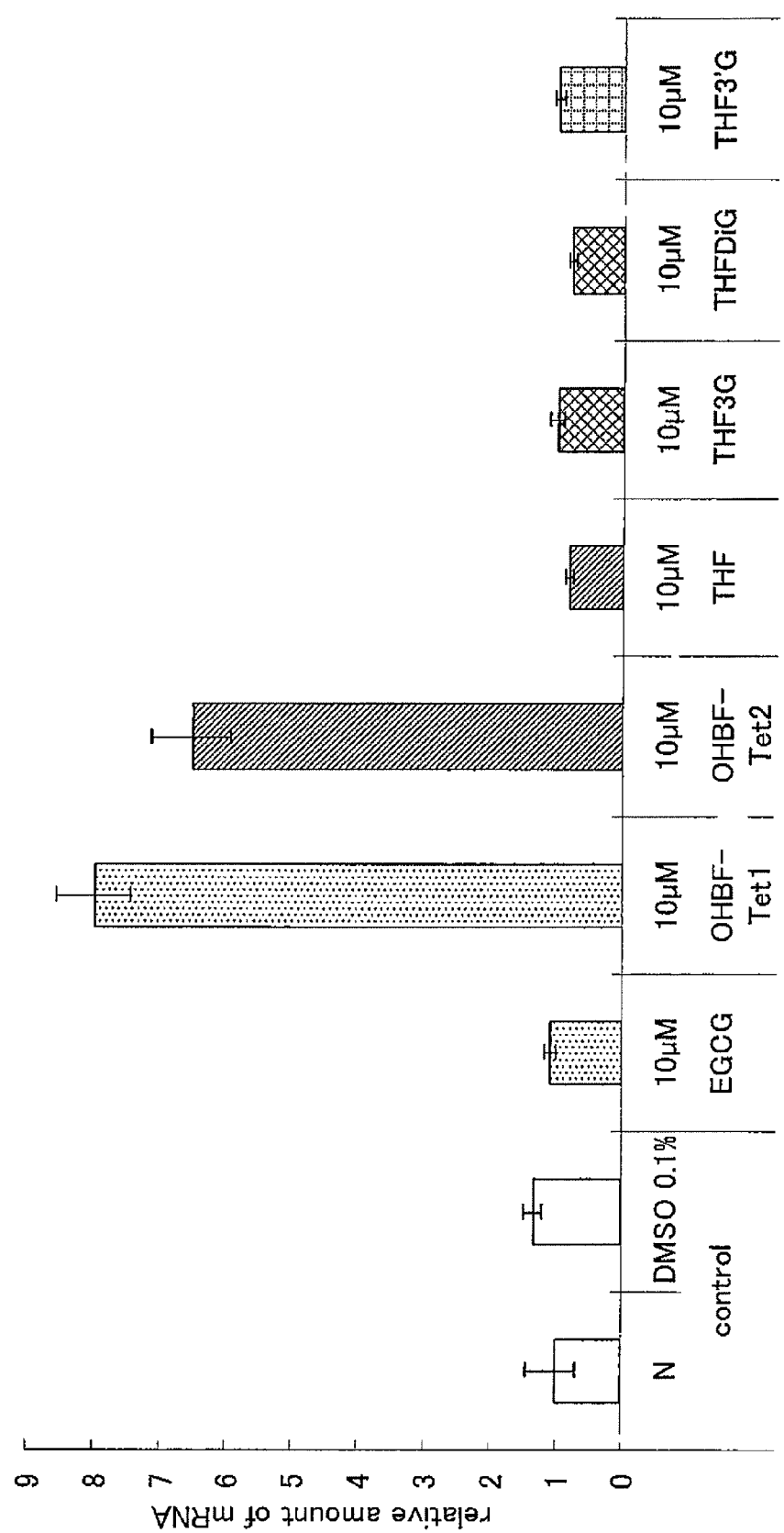
FIG. 6 is a graph showing the results of GTP-CH1 expression.

NMR was measured in the following conditions. Compound 1 and compound 2 were each dissolved in DMSO-d6 ((CD₃)₂SO) and NMR measurement was performed using residual peaks of ¹H and ¹³C, i.e., δ2.50 and δ39.43, as the internal standard. Measurement items, which were ¹H NMR, ¹³C NMR, 1H{¹³C}-HSQC, ¹H{¹³C}HMBC, TOCSY and DQF-COSY, were measured by DMX-750 spectrometer (BRUKER BIOSPIN, Germany). As a result of the NMR, it was elucidated that compound 1 is a compound (Formula (II)) having a coupling scheme of EGCG8:8 EGCG6:8 EGCG6:8 EGCG and compound 2 is a compound (Formula (III)) having a coupling scheme of EGCG8:6 EGCG8:8 EGCG6:8 EGCG. The ¹H NMR and ¹³C NMR spectra of compound 1 are shown in FIGS. 1 and 2 and the ¹H NMR and ¹³C NMR spectra of compound 2 are shown in FIGS. 3 and 4, respectively.

Compound 1:

Signals of $^1$H NMR (in DMSO-d6) observed were δ 10.34, 9.37, 9.17, 9.09, 9.01, 8.88, 8.75, 8.71, 8.68, 8.08, 8.04, 7.62, 6.81, 6.77, 6.72, 6.55, 6.49, 6.39, 6.04, 5.86, 5.55, 5.47, 5.34, 5.23, 4.96, 4.79, 4.64, 4.04, 4.02, 3.92, 3.90, 3.85, 3.83, 3.73, 3.71, 3.64, 3.62, 3.54, 3.52, 3.07, 3.05, 2.96, 2.93, 2.74, 2.72, 2.70.

Signals of $^{13}$C NMR observed were δ 165.29, 165.13, 165.02, 165.01, 154.45, 154.44, 154.25, 152.33, 152.20, 151.97, 151.66, 151.62, 150.82, 150.66, 150.52, 149.66, 145.63, 145.56, 145.54, 145.50, 145.50, 145.27, 145.23, 145.18, 138.46, 138.38, 132.77, 132.26, 132.12, 128.50, 127.61, 119.20, 119.17, 118.96, 118.90, 108.73, 108.55, 107.05, 106.19, 105.19, 105.05, 104.31, 103.77, 99.01, 98.52, 77.44, 76.65, 76.51, 76.10, 67.53, 67.50, 66.95, 66.63, 25.94, 25.63, 25.49, 25.30, 17.14, 16.74, 15.81.

Compound 2:

Signals of $^1$H NMR (in DMSO-d6) observed were δ 9.91, 9.25, 9.16, 8.09, 7.22, 6.81, 6.76, 6.74, 6.52, 5.94, 5.50, 5.38, 4.77, 4.52, 3.95, 3.95, 3.80, 3.54, 2.80, 2.74, 2.73, 2.67.

Signals of $^{13}$C NMR observed were δ 165.08, 165.01, 154.06, 152.83, 152.35, 151.45, 150.78, 150.26, 145.52, 145.52, 145.24, 145.18, 138.49, 138.44, 132.21, 132.10, 128.42, 127.63, 119.05, 118.95, 108.58, 108.46, 108.46, 106.95, 105.74, 104.92, 104.06, 98.32, 97.81, 76.59, 75.94, 66.69, 66.35, 26.33, 25.26, 16.72, 15.99.

The yields of the individual compounds obtained by the aforementioned synthesis and purification were as follows: compound 3 (oolong homobisflavan A, 984 mg), compound 4 (oolong homobisflavan-B, 374 mg), compound 5 (468 mg), compound 6 (oolong homobisflavan-C, 33 mg), compound 1 (15 mg) and compound 2 (44 mg).

Example 2

Study on Vascular Endothelial Function Improving Effect Using Cultured Vascular Endothelial Cell (A) Vascular Endothelial Function Improving Effect of Formula (II) and Formula (III)

With respect to the compounds of Formula (II) and Formula (III) synthesized and purified in Example 1, the effect of them on expression of a gene involved in the vascular endothelial function was studied. Furthermore, as compounds for comparison, an EGCG monomer (manufactured by Wako Pure Chemical Industries Ltd.), theaflavin, theaflavin 3-O-gallate, theaflavin 3'-O-gallate and theaflavin 3,3'-O-digallate (manufactured by Nagara Science Co., Ltd.), which are known to have a vascular endothelial function improving action.

These compounds were dissolved in sterilized dimethyl sulfoxide (DMSO, manufactured by Nacalai Tesque Inc.) to prepare a solution having a concentration of 10 mM.

These solutions were diluted 1000 fold by using HuMedia-EG2 medium (manufactured by Kurabo Industries Ltd.) to prepare a solution having a final concentration of 10 μM (the final concentration of DMSO was 0.1 V/V %). These sample solutions each were added to human umbilical vascular endothelial cells (manufactured by Kurabo Industries Ltd.) cultured in a 6-well plate in a proportion of 3 mL/well and incubated at 37° C. under 5% $CO_2$ conditions for 8 hours.

The cells were recovered by ISOGEN (manufactured by Nippon Gene Co., Ltd.) and RNA was extracted from the cells. Furthermore, RNA was purified by RNeasy Mini Kit (QIAGEN). cDNA was synthesized by a High-Capacity cDNA reverse transcription kit (manufactured by Applied Biosystem) using the total RNA (200 ng) purified as a template and quantitative PCR was performed. Analysis was performed by comparative Ct method with a glyceraldehyde-3-phosphate dehydrogenase gene used as an internal standard. The gene expression change ratio (ratio relative to the control) of a test sample was calculated by using untreated cells as a control.

The expression change rates of individual genes, i.e., EGCG, Formula (II)(OHBF-Tet1), Formula (III)(OHBF-Tet2), theaflavin (THF), theaflavin 3-O-gallate (THF3G), theaflavin 3'-O-gallate (THF3'G) and theaflavin 3,3'-O-digallate (THFDiG) are shown in FIGS. 5 to 8.

Figure 7:
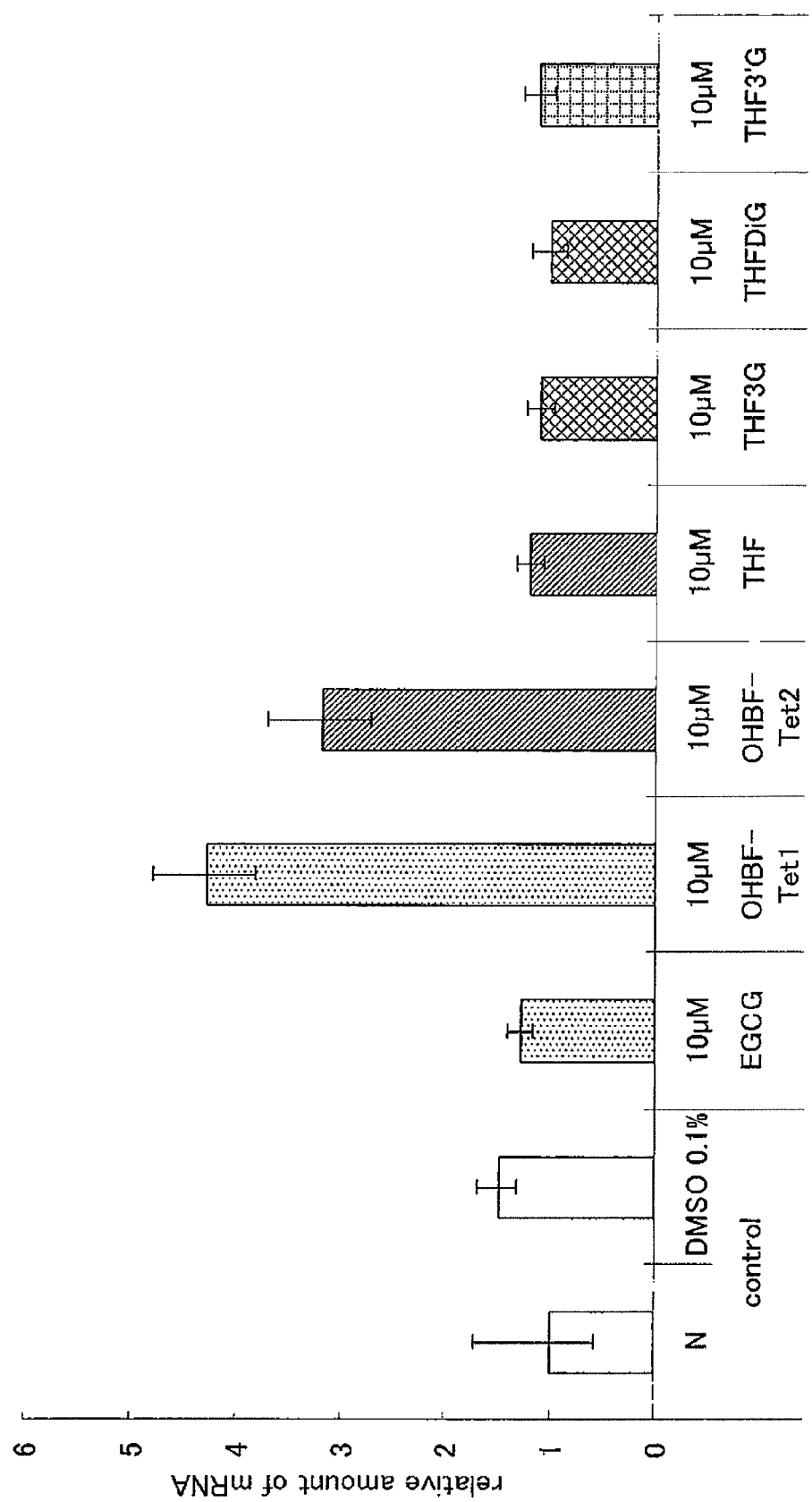
FIG. 7 is a graph showing the results of DDAH2 expression.
Figure 8:
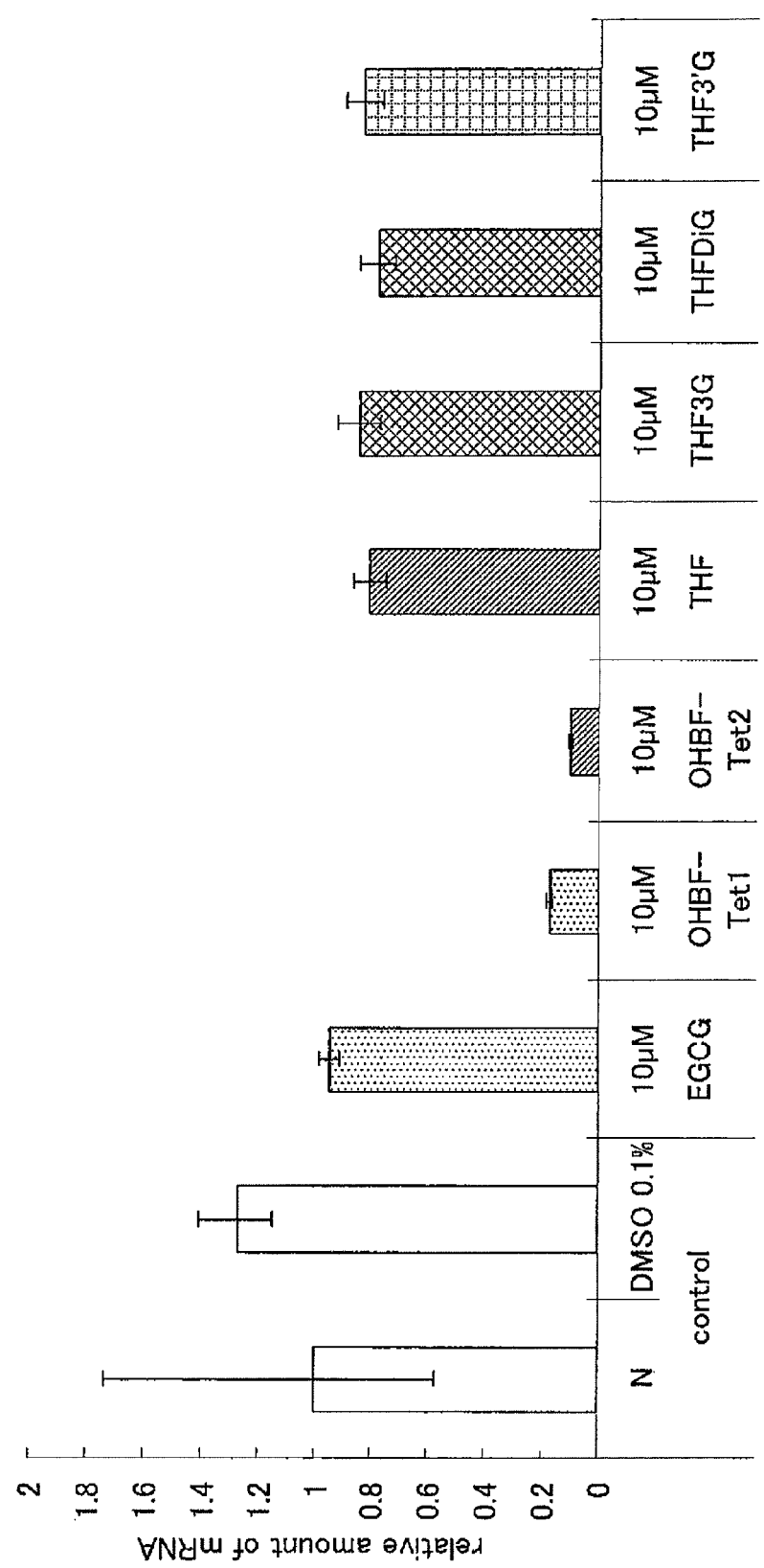
FIG. 8 is a graph showing the results of expression of Nox4 subunit gene of NADPH oxidase.
Figure 9:
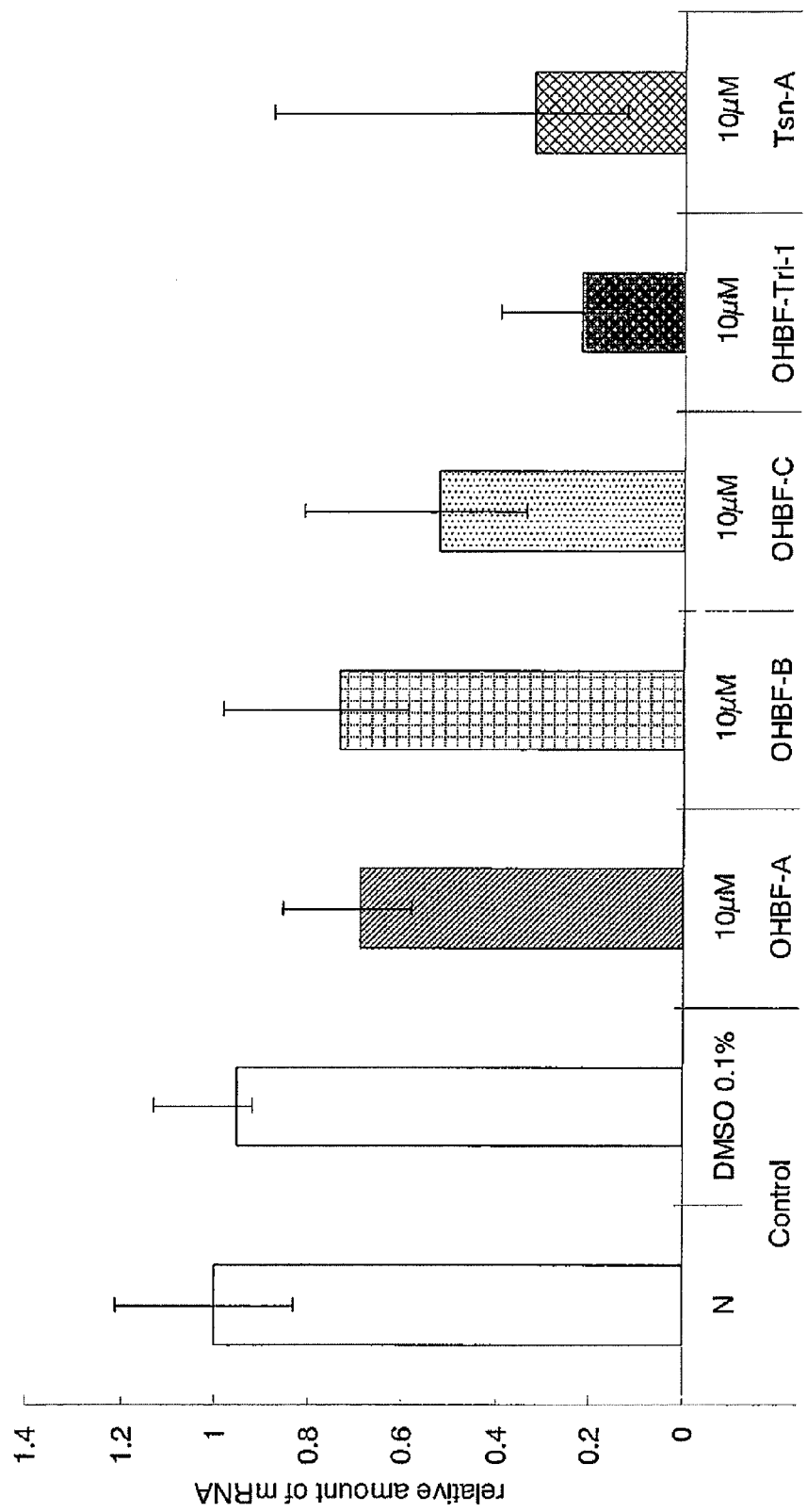
FIG. 9 is a graph showing the results of eNOS expression.
Figure 10:
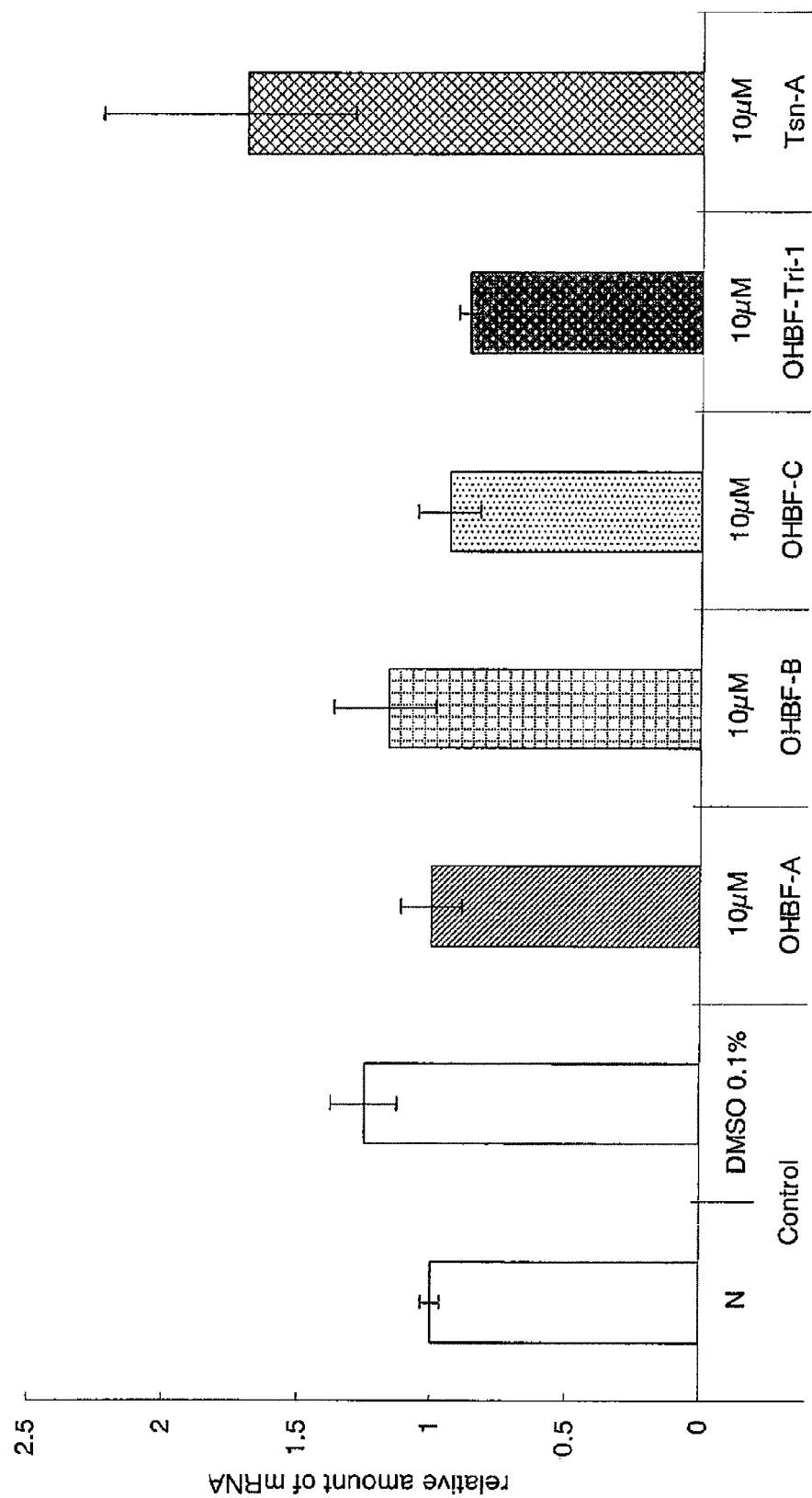
FIG. 10 is a graph showing the results of GTP-CH1 expression.
Figure 11:
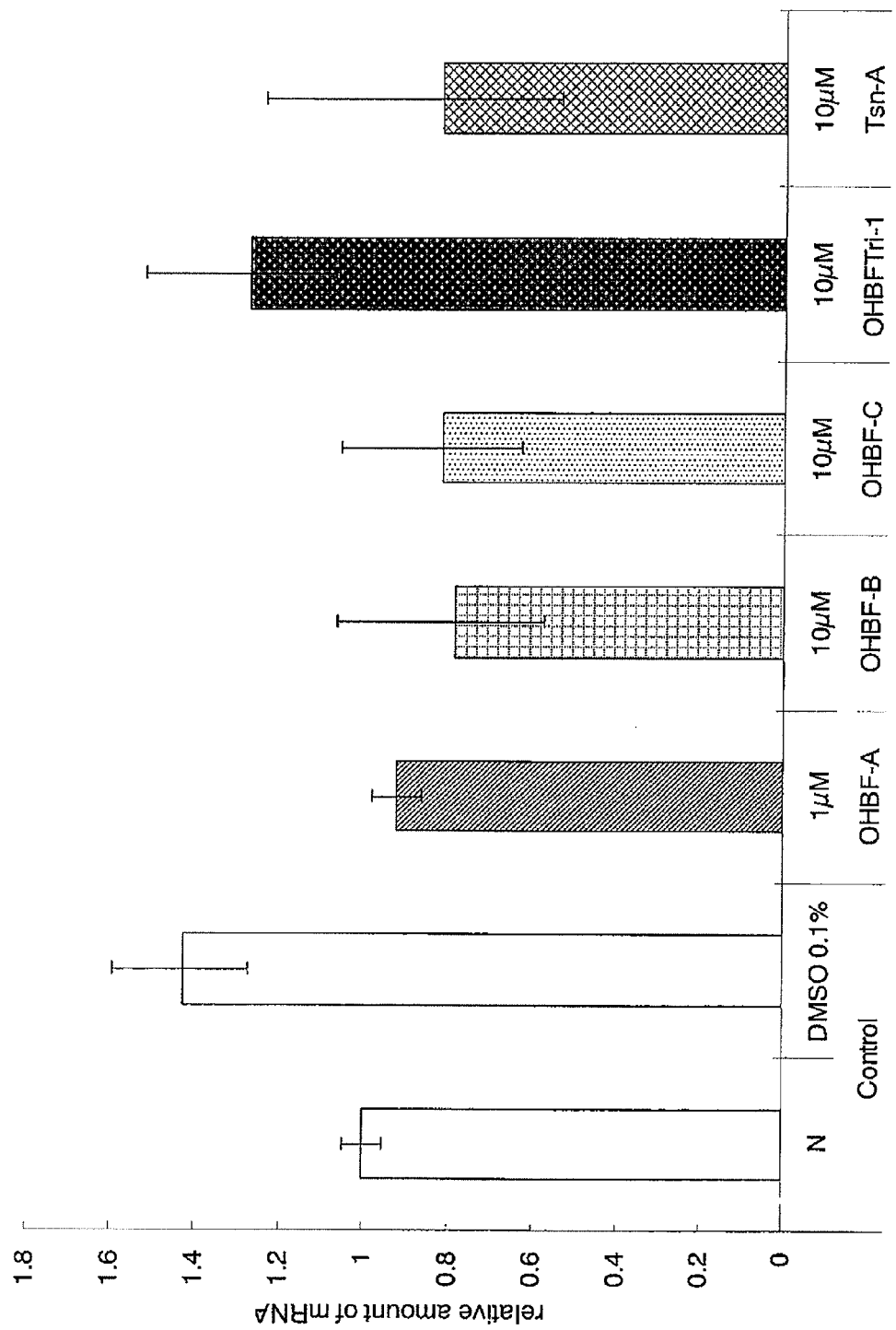
FIG. 11 is a graph showing the results of DDAH2 expression.
Figure 12:
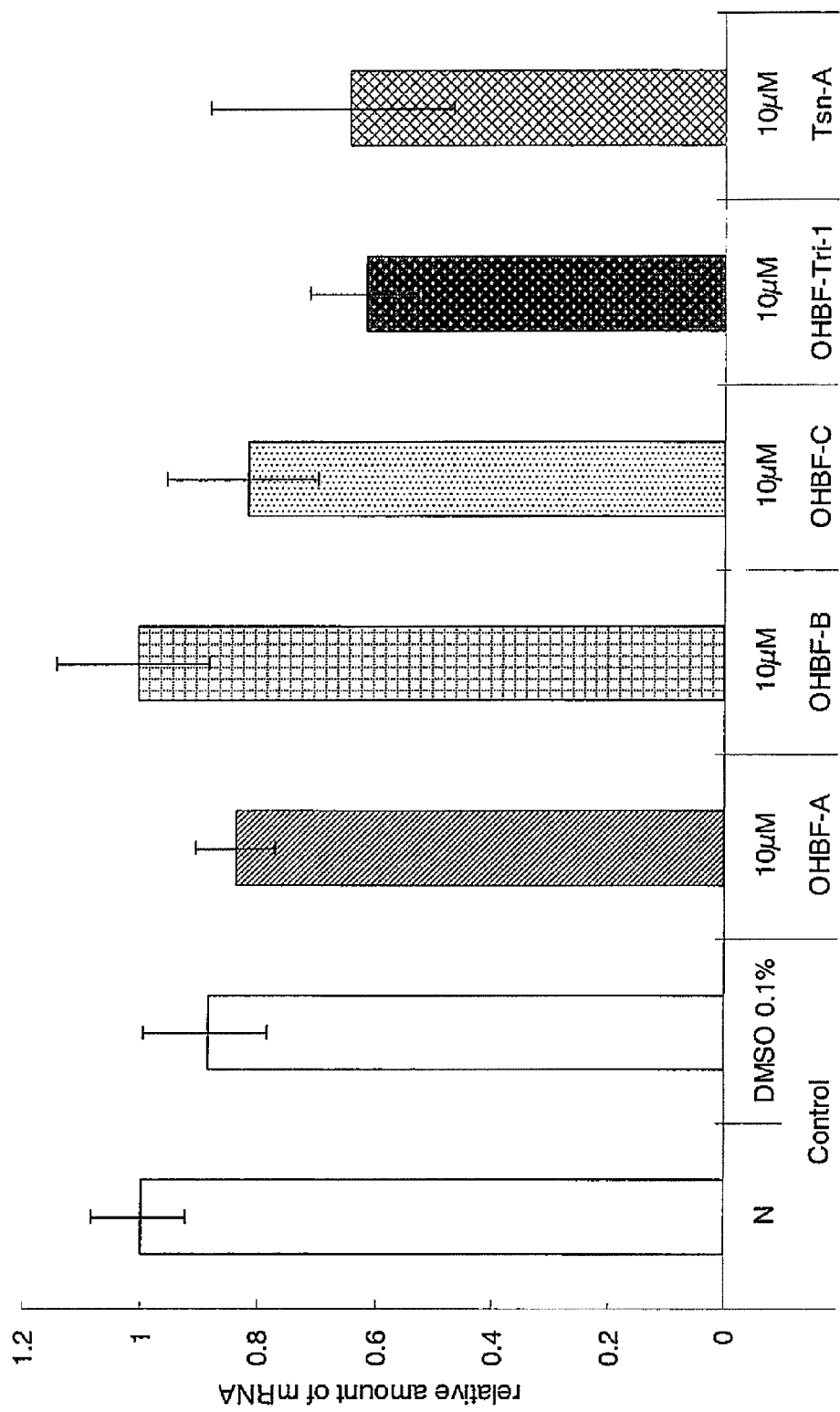
FIG. 12 is a graph showing the results of expression of Nox4 subunit gene of NADPH oxidase.

The compounds of Formula (II) and Formula (III) enhanced expression of the eNOS gene about three times (FIG. 5), the expression of the GTP-CH1 gene about 7 times (FIG. 6) and the expression of the DDAH2 gene about three times (FIG. 7). Furthermore, it is shown that expression of Nox4 subunit gene of NADPH oxidase producing active oxygen in the vascular endothelial cells and reducing vascular endothelial function dramatically reduces in the presence of the compounds of Formula (II) and Formula (III) (FIG. 8).

On the other hand, it was elucidated that an EGCG monomer and theaflavins in concentrations investigated herein do not substantially change expression of all genes and that the EGCG tetramer of the present invention is effective in a lower concentration than the EGCG monomer and theaflavins.

(B) Vascular Endothelial Function Improving Effect of EGCG Polymers

Effect of an EGCG dimer and trimer upon expression of vascular endothelial function related gene was investigated. Of the EGCG polymers used in evaluation, theasinensin (TSN)-A is the one synthesized in accordance with the paper (Hashimoto, F. Nonaka, G. Nishioka, I. Chem. Pharm. Bull. 36 (5), 1676-1684 (1988)). Oolong homobisflavan-A, oolong homobisflavan-B, oolong homobisflavan-C and compound 5 used herein were those synthesized and purified in Example 1. Evaluation was performed in the same method as in the above (A).

The expression change ratios of individual genes of oolong homobisflavan-A (OHBF-A), oolong homobisflavan-B (OHBF-B), oolong homobisflavan-C(OHBF-C), compound 5 (OHBFTri-1) and theasinensin-A (TSN-A) are shown in FIGS. 9 to 12.

As shown in FIGS. 9 to 12, EGCG dimers, i.e., oolong homobisflavan-A, oolong homobisflavan-B, oolong homobisflavan-C, theasinensin A and an EGCG trimer, i.e., compound 5, do not substantially change the expression of any one of the genes in the same concentration as in the compounds of Formula (II) and Formula (III) investigated in the above (A).

From the above results, it was found that the vascular endothelial function improving effect of the EGCG tetramer of the present invention is a characteristic function of a compound of the present invention among EGCG polymers.

Example 3

LC-MS/MS Measurement Conditions and Measurement of Suntory Black Oolong Tea

LC-MS/MS was measured by 4000 Q TRAP (manufactured by Applied) using a turbo ion spray in a negative mode in the following conditions: Collision energy: 46 eV (nega.), Ionspray voltage: 4500V, Temp: 450° C.

As a measurement channel in MRM (multiple reaction monitoring), 933.16/168.90 (nega. divalent) was used for an EGCG tetramer compound. The measurement was performed in the following conditions. The compound of Formula (III) was used as a standard substance.

Column: Develosil C30-UG-3 (manufactured by Nomura Chemical Co., Ltd., 3 mmφ×150 mm)
Flow rate: 0.3 mL/minute
Column temperature: 40° C.

Mobile phase A: 0.1 V/V % HCOOH/H$_2$O
Mobile phase B: 0.1 V/V % HCOOH/CH$_3$CN
Gradient program: A/B=91/9 (0 minute)→A/B=40/60 (17 minutes)→A/B=15/85 (17.1 minutes)→A/B=15/85 (17.1 minutes to 19 minutes)

Using the above conditions, Suntory black oolong tea was measured.

The Suntory black oolong tea blend (solution before sterilized) was fractionated stepwise by a CHP-20P column (manufactured by Mitsubishi Chemical Corporation) and fractions were quantified. The concentrations of individual fractions detected were added up and defined as the concentration in the blend. The concentration in the blend was obtained by adding up the concentrations of 4 components detected as an EGCG tetramer. It was 55 ng/mL in terms of the compound of Formula (III).

The invention claims is:

1. A composition comprising a compound represented by Formula (I):

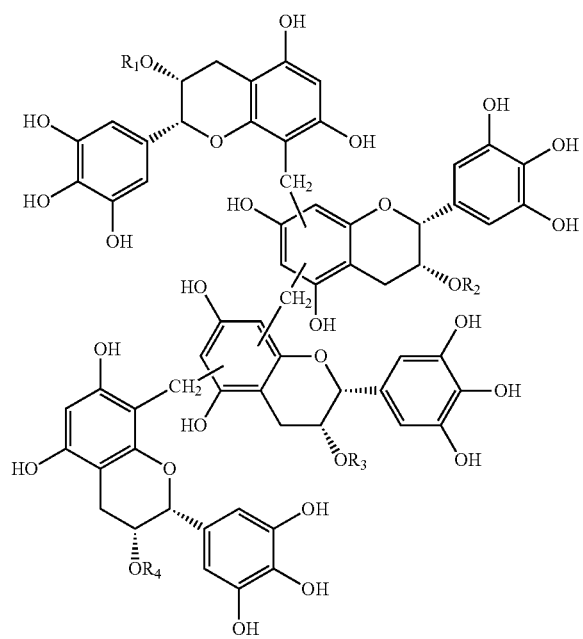

(I)

wherein R$_1$, R$_2$, R$_3$ and R$_4$ are each independently H or a group represented by Formula (A):

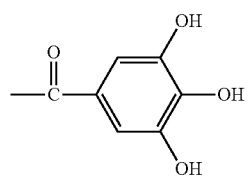

Formula (A)

or a salt thereof at a concentration of 0.06 to 2000 ppm.

2. A food and drink, comprising a compound represented by formula (I):

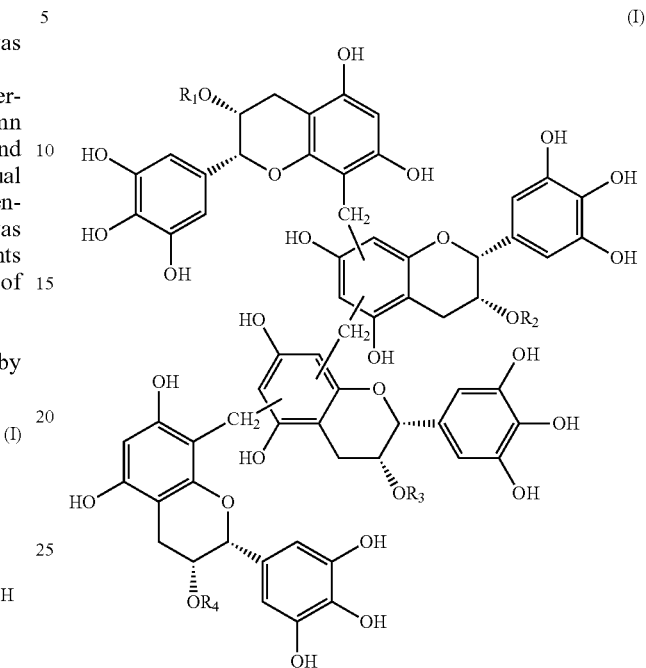

(I)

wherein R$_1$, R$_2$, R$_3$ and R$_4$ are each independently H or a group represented by Formula (A):

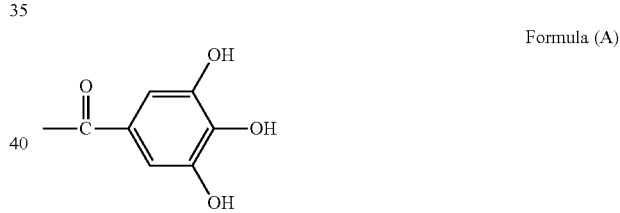

Formula (A)

or a salt thereof at a concentration of 0.06 to 2000 ppm.

3. The composition of claim 1, further comprising a pharmaceutically acceptable carrier, wherein said composition is a pharmaceutical composition.

4. The composition of claim 1, wherein concentration is from 0.1 to 1000 ppm.

5. The food or drink of claim 2, wherein concentration is from 0.1 to 1000 ppm.

6. The pharmaceutical composition of claim 3, wherein concentration is from 0.1 to 1000 ppm.

* * * * *